United States Patent
Iida

(10) Patent No.: US 11,607,483 B2
(45) Date of Patent: Mar. 21, 2023

(54) BLOOD SEPARATION METHOD AND BLOOD SEPARATION FILTER

(71) Applicant: TERUMO KABUSHIKI KAISHA, Tokyo (JP)

(72) Inventor: Naoki Iida, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 777 days.

(21) Appl. No.: 16/495,786

(22) PCT Filed: Mar. 22, 2018

(86) PCT No.: PCT/JP2018/011519
§ 371 (c)(1),
(2) Date: Sep. 19, 2019

(87) PCT Pub. No.: WO2018/174195
PCT Pub. Date: Sep. 27, 2018

(65) Prior Publication Data
US 2020/0022871 A1    Jan. 23, 2020

(30) Foreign Application Priority Data
Mar. 24, 2017  (JP) .............................. JP2017-058366

(51) Int. Cl.
*A61M 1/38* (2006.01)
*A61M 1/36* (2006.01)
(Continued)

(52) U.S. Cl.
CPC ............ *A61M 1/38* (2013.01); *A61M 1/3633* (2013.01); *A61J 1/10* (2013.01); *A61J 1/2079* (2015.05);
(Continued)

(58) Field of Classification Search
CPC .... A61J 1/2079; A61M 1/38; A61M 2206/10; A61M 1/3635; A61M 1/3636; A61M 1/3633
See application file for complete search history.

(56) References Cited

U.S. PATENT DOCUMENTS

2003/0173274 A1   9/2003   Corbin et al.
2005/0051486 A1   3/2005   Zuk, Jr.

FOREIGN PATENT DOCUMENTS

EP    1238694 A2 *  9/2002   .......... A61M 1/3633
JP    2000-180440   6/2000
(Continued)

OTHER PUBLICATIONS

Official Action (with machine translation) for China Patent Application No. 2018800189096, dated Oct. 27, 2021, 12 pages.
(Continued)

*Primary Examiner* — Leslie R Deak
(74) *Attorney, Agent, or Firm* — Sheridan Ross P.C.

(57) ABSTRACT

A blood separation method using a blood separation filter (10A) includes: an arrangement step of arranging a housing (18) such that a blood inflow chamber (20) is positioned below a filter member (24) and the blood outflow chamber (22) is positioned above a filter medium (38); a blood treatment step of allowing blood to flow in the filter medium (38) upward from vertically below; and a post residual treatment blood collection step of arranging the housing (18) such that an outflow port (28) is positioned vertically below the blood outflow chamber (22) so as to guide the post-separation residual blood in the housing (18) to the outflow port (28).

20 Claims, 12 Drawing Sheets

(51) Int. Cl.
    *A61J 1/20*          (2006.01)
    *A61J 1/10*          (2006.01)

(52) U.S. Cl.
    CPC ............... *A61M 2202/0427* (2013.01); *A61M 2202/0439* (2013.01); *A61M 2206/10* (2013.01)

(56) References Cited

FOREIGN PATENT DOCUMENTS

| | | |
|---|---|---|
| JP | 2001-500053 | 1/2001 |
| JP | 2005237791 A | 9/2005 |
| WO | 98/01207 | 1/1998 |
| WO | 2010/026891 | 3/2010 |

OTHER PUBLICATIONS

International Search Report and Written Opinion (with English translation) for International (PCT) Patent Application No. PCT/JP2018/011519, dated May 15, 2018, 11 pages.

Official Action (with machine translation) for China Patent Application No. 201880018909.6, dated Jun. 15, 2022, 13 pages.

\* cited by examiner

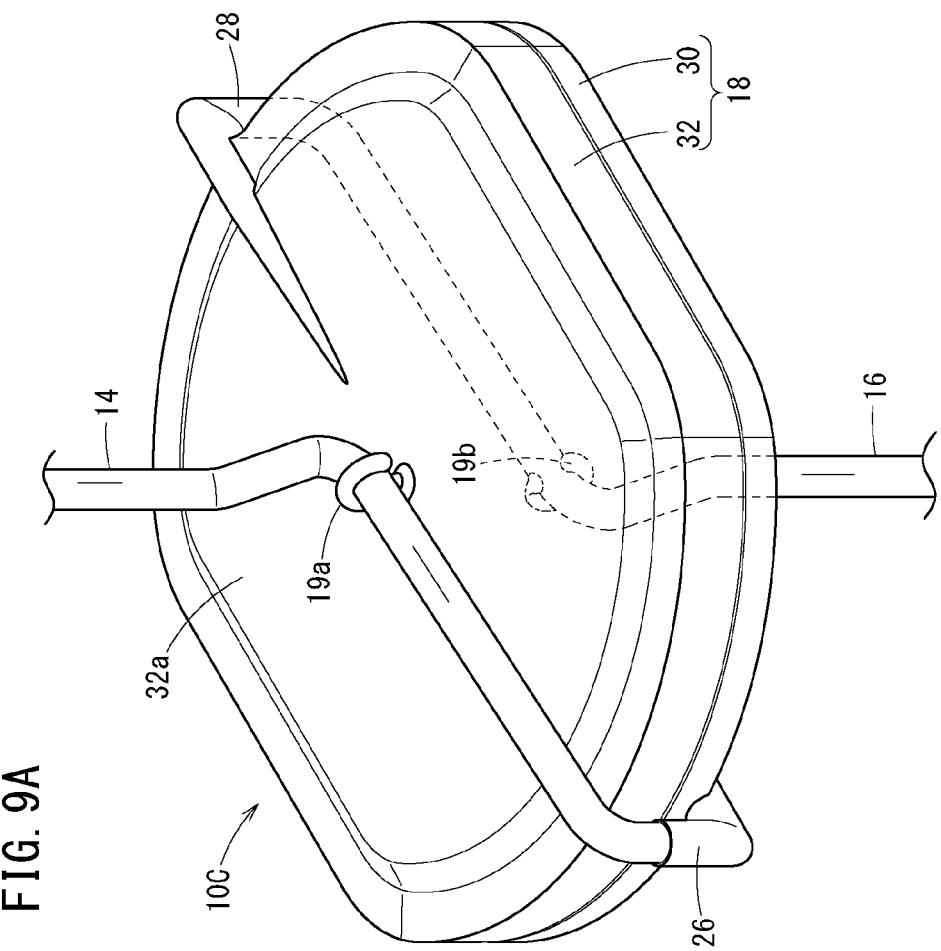
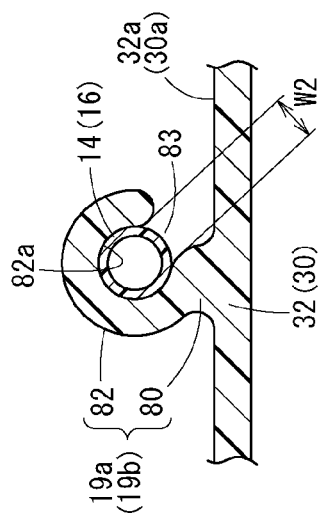

BLOOD SEPARATION METHOD AND BLOOD SEPARATION FILTER

TECHNICAL FIELD

The present invention relates to a blood separation method and a blood separation filter for separating a predetermined blood component from blood.

BACKGROUND ART

Blood separation filters have been conventionally used to separate a predetermined blood components (white blood cells or platelets, for example) from the blood collected from a donor. The blood separation filter includes a housing; a filter medium that partitions interior of the housing into a blood inflow chamber and a blood outflow chamber in a thickness direction; an inflow port that allows the blood to flow into the blood inflow chamber; and an outflow port that allows post-separation blood from which a blood component has been separated via the filter medium to flow out from the interior of the blood outflow chamber (refer to re-publication WO 2010/026891, for example).

In the case of using such a blood separation filter, a blood bag containing blood before separation (before filtration) is suspended from a suspension base. In this state, the housing is vertically arranged such that the inflow port comes at an upper position and the outflow port comes at a lower position, and the filter medium is used to filter the blood guided from the blood bag to the blood separation filter by the gravitational force.

SUMMARY OF INVENTION

The conventional blood separation filter, however, has a disadvantage that the arrangement of the housing in the vertical direction causes accumulation of blood at a lower side of the interior of the blood inflow chamber by an effect of gravity at the time of separating blood components from the blood. This would hinder effective use of the upper side of the filter medium, reducing the effective area of the filter medium. Reduction in the effective area of the filter medium might lead to a decrease in flow rate, leakage of blood components, clogging of filtration, hemolysis, or the like, during filtration.

In addition, in a case where the housing is horizontally arranged such that the blood inflow chamber is positioned above the blood outflow chamber, the blood flowing into the blood inflow chamber from the inflow port starts to be filtered downward before spreading over the entire surface of the filter medium. This might lead to air (bubbles) stagnation on the surface of the filter medium, also referred to as air block. This would hinder filtering of blood at a place of air stagnation in the filter medium, causing reduction of the effective area of the filter medium.

The present invention is made in view of these problems and aims to provide a blood separation method and a blood separation filter capable of preventing the reduction in effective area of the filter medium.

In order to achieve the above object, the blood separation method according to the present invention is a blood separation method using a blood separation filter that separates a predetermined blood component from blood, the blood separation filter including: a housing; a filter medium disposed in the housing and partitioning the housing into a blood inflow chamber and a blood outflow chamber in a thickness direction of the housing; an inflow port provided in the housing to allow blood to flow into the blood inflow chamber; and an outflow port provided in the housing to allow post-separation blood from which a blood component has been separated by the filter medium to flow out from the blood outflow chamber, the blood separation method including: an arrangement step of arranging the housing such that the blood inflow chamber is positioned vertically below the filter medium and the blood outflow chamber is positioned vertically above the filter medium; a blood treatment step of first allowing the blood to flow from the inflow port into the blood inflow chamber in a state of the arrangement step, allowing the blood to flow through the inside of the filter medium upward from vertically below, and then allowing the post-separation blood inside the blood outflow chamber to flow out to the outflow port; and a post residual treatment blood collection step of arranging the housing such that the outflow port is positioned vertically below the blood outflow chamber after the blood treatment step, thereby guiding post-separation residual blood in the housing to the outflow port.

According to such a method, the blood flowing into the blood inflow chamber from the inflow port spreads to the entire portions inside the blood inflow chamber, and then the blood liquid level rises to come in contact with substantially the entire surface (lower surface) of the filter medium. Thereafter, the blood passes through the filter medium upward from below so as to be guided to the blood outflow chamber. This makes it possible to suppress nonuniformity of blood in the blood inflow chamber. In addition, it is possible to reliably discharge the air from the blood inflow chamber, leading to suppression of occurrence of air block. This makes it possible to prevent the reduction of the effective area of the filter medium. Moreover, the housing is arranged after the blood treatment step, making it possible to efficiently collect the post-separation residual blood in the housing.

In the above-described blood separation method, the housing may include an inlet-side retainer to which an inflow tube connected to the inflow port is detachably mounted, the arrangement step may arrange the housing in a state where the inflow tube is mounted to the inlet-side retainer, and the post residual treatment blood collection step may arrange the housing by detaching the inflow tube from the inlet-side retainer.

According to such a method, it is possible to easily switch the housing from a state perpendicular to the vertical direction (a laid-down state) to a state horizontal to the vertical direction (upright state).

In the above-described blood separation method, the inlet-side retainer may be provided at a center portion of an outer surface of the housing on a side where the blood outflow chamber is located, and the arrangement step may allow at least a portion of the inflow tube to extend on a center-of-gravity line passing through center-of-gravity of the blood separation filter in a state where the inflow tube is mounted to the inlet-side retainer.

According to such a method, it is possible to arrange the housing in a laid-down state close to the horizontal posture in the arrangement step.

In the above-described blood separation method, an outlet-side retainer to which an outflow tube connected to the outflow port is detachably mounted may be provided at a center portion of an outer surface of the housing on a side where the blood inflow chamber is located, and the arrangement step may allow at least a portion of the outflow tube to extend on the center-of-gravity line in a state where the outflow tube is mounted to the outlet-side retainer.

According to such a method, it is possible to arrange the housing in a laid-down state closer to the horizontal posture in the arrangement step.

In the above-described blood separation method, the post residual treatment blood collection step may detach the outflow tube from the outlet-side retainer.

According to such a method, it is possible to efficiently collect the post-separation residual blood in the housing via the outflow tube.

A blood separation filter according to the present invention is a blood separation filter that separates a predetermined blood component from blood, the blood separation filter including: a housing; a filter medium disposed in the housing and partitioning interior of the housing into a blood inflow chamber and a blood outflow chamber in a thickness direction of the housing; an inflow port provided in the housing to allow blood to flow into the blood inflow chamber; and an outflow port provided in the housing to allow post-separation blood from which a blood component has been separated by the filter medium to flow out from the blood outflow chamber, in which the inflow port is connected with an inflow tube, the housing includes an inlet-side retainer to which the inflow tube is detachably attached, the housing is arranged, in a state where the inflow tube is mounted to the inlet-side retainer, such that the blood inflow chamber is positioned vertically below the filter medium and the blood outflow chamber is positioned vertically above the filter medium, and the housing is arranged, in a state where the inflow tube has been detached from the inlet-side retainer, such that the outflow port is positioned vertically below the blood outflow chamber.

According to such a configuration, it is possible to obtain a blood separation filter capable of obtaining an effect similar to the case of the above-described blood separation method.

In the above-described blood separation filter, the housing may include a first outer surface on a side where the blood inflow chamber is located and a second outer surface on a side where the blood outflow chamber is located, the inlet-side retainer may be provided at a center portion of the second outer surface, and the inlet-side retainer may be configured such that at least a portion of the inflow tube is extendable on a center-of-gravity line passing through center-of-gravity of the blood separation filter in a state where the housing is arranged with the inflow tube being mounted on the inlet-side retainer.

According to such a configuration, it is possible to easily arrange the housing in a laid-down state close to the horizontal posture.

In the above-described blood separation filter, an outflow tube may be connected to the outflow port, an outlet-side retainer to and from which the outflow tube is attachable and detachable may be provided at a center portion of the first outer surface, and the outlet-side retainer may be configured to allow at least a portion of the outflow tube to extend on the center-of-gravity line in a state where the outflow tube is mounted to the outlet-side retainer.

According to such a configuration, it is possible to easily arrange the housing in a laid-down state close to the horizontal posture.

In the above-described blood separation filter, at least one of the inlet-side retainer and the outlet-side retainer may be a clip portion having a retainer groove to and from which the inflow tube or the outflow tube is attachable and detachable.

According to such a configuration, the inflow tube can be attached or detached to or from the inlet-side retainer with a simple configuration, and the outflow tube can be attached or detached to or from the outlet-side retainer with a simple configuration.

In the above-described blood separation filter, at least one of the inlet-side retainer and the outlet-side retainer is a hook portion capable of hooking the inflow tube or the outflow tube.

In the above-described blood separation filter, at least one of the inlet-side retainer and the outlet-side retainer is a strip-shaped member removably joined to the housing so as to form, between the strip-shaped member and the housing, a space through which the inflow tube or the outflow tube can be inserted.

According to the present invention, the housing is arranged in a laid-down state so that the blood inflow chamber is positioned below the filter medium and the blood outflow chamber is positioned above the filter medium. Accordingly, it is possible to suppress nonuniformity of blood in the blood inflow chamber, leading to suppression of occurrence of air block. This makes it possible to prevent the reduction of the effective area of the filter medium. In addition, the housing is arranged in an upright posture after blood transfer, making it possible to efficiently collect the post-separation residual blood in the housing.

BRIEF DESCRIPTION OF DRAWINGS

FIG. 9A is a perspective view of a blood separation filter according to a third embodiment of the present invention. FIG. 9B is an enlarged cross-sectional view of an inlet-side retainer (outlet-side retainer) of FIG. 9A.

DESCRIPTION OF EMBODIMENTS

Hereinafter, preferred embodiments of the blood separation method and blood separation filter according to the present invention will be described with reference to the accompanying drawings.

First Embodiment

Figure 1:
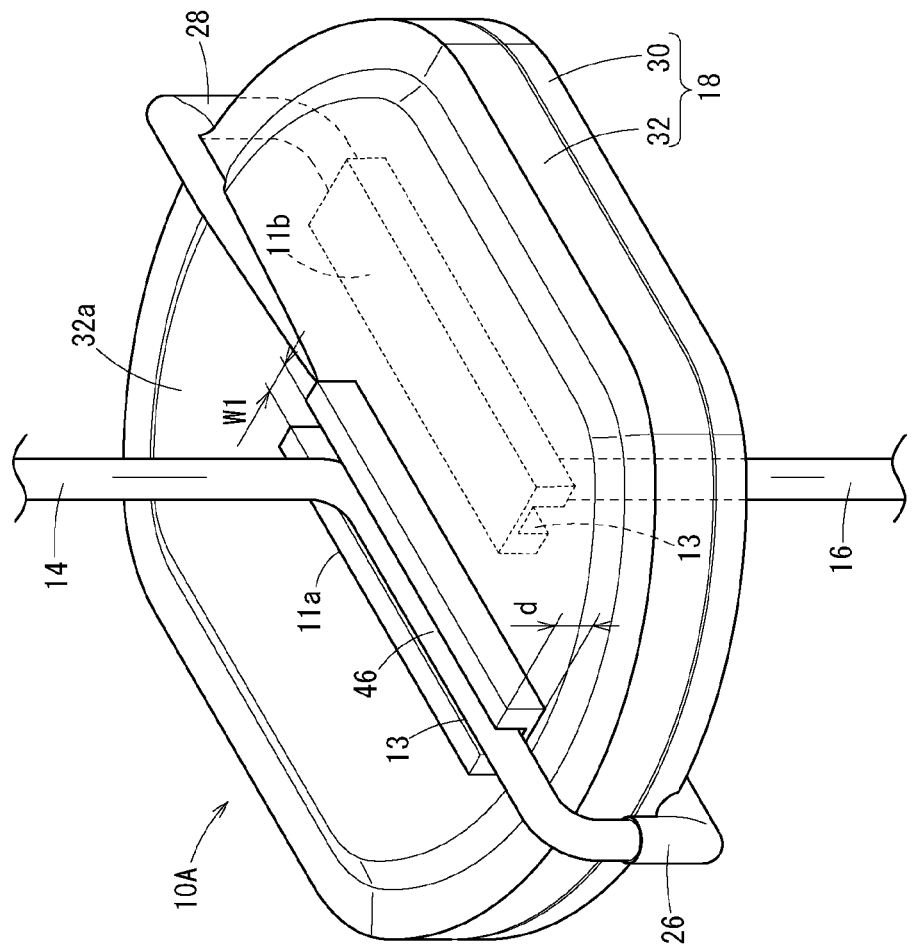
FIG. 1 is a perspective view of a blood separation filter according to a first embodiment of the present invention.

A blood separation filter 10A illustrated in FIG. 1 is a filter that separates or removes a predetermined blood component such as white blood cells or platelets from the blood. The blood separation filter 10A is equipped with an inflow tube 14 that guides blood into a housing 18 and an outflow tube 16 that guides the blood from the interior of the housing 18.

Figure 2:
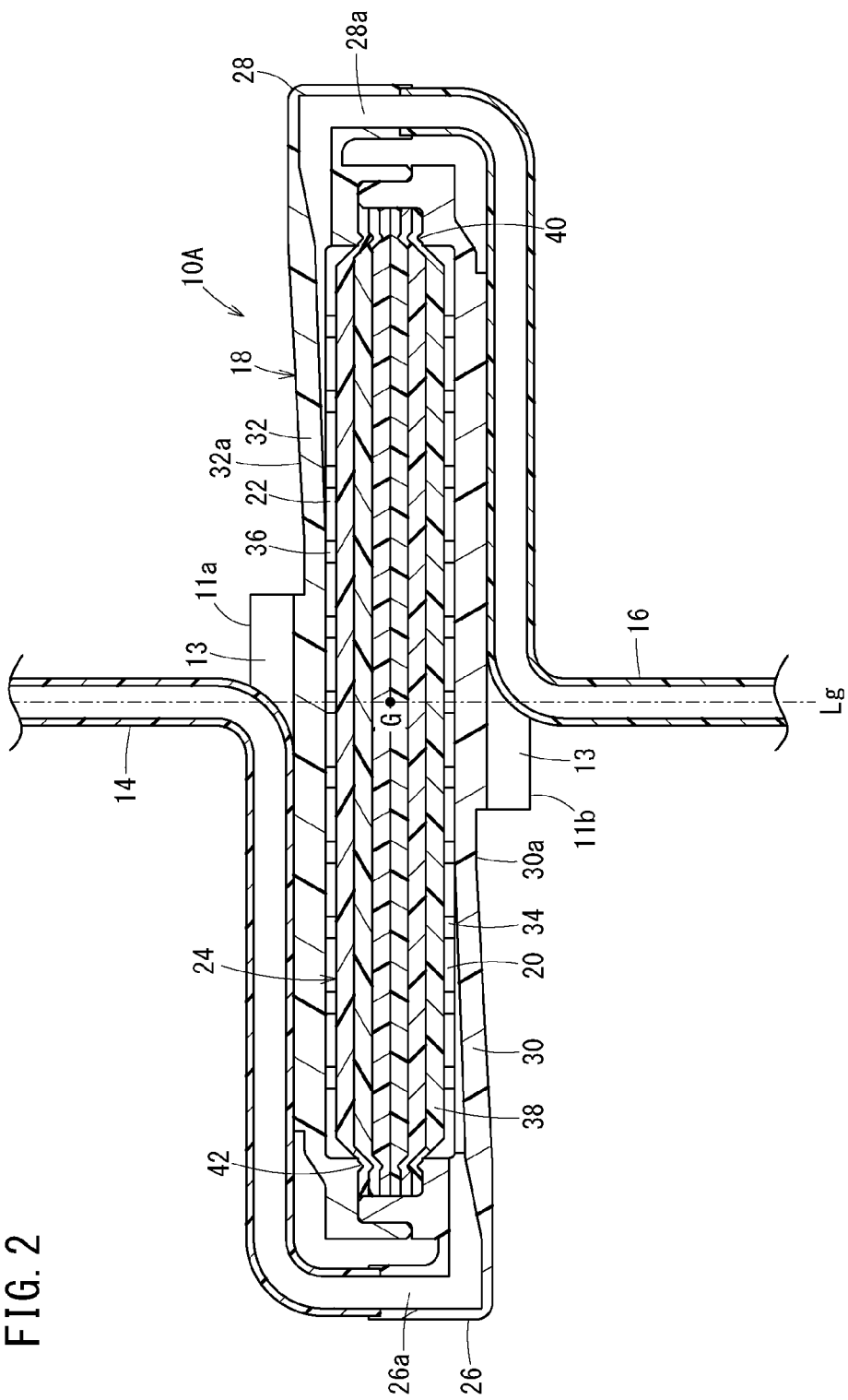
FIG. 2 is a longitudinal sectional view of the blood separation filter of FIG. 1.

As illustrated in FIG. 2, the blood separation filter 10A includes: the housing 18; a filter member 24 that partitions interior of the housing 18 in an up-down direction (thickness direction orthogonal to the extending direction of the housing 18) into a blood inflow chamber 20 and a blood outflow chamber 22 and that includes a filter medium 38; an inflow port 26 that allows blood to flow into the blood inflow chamber 20; and an outflow port 28 that allows blood from which a blood component has been separated (post-separation blood) by the filter member 24 to flow out from the blood outflow chamber 22.

In FIGS. 1 and 2, the housing 18 has a shape in a plan view in which each of short sides of a rectangle protrudes in an arc shape. That is, the housing 18 extends in a planar shape. The housing 18 is arranged horizontally in use and has a pair of resin cases (a first case 30 and a second case 32) that constitutes mutually opposite walls. Each of the first case 30 and the second case 32 is formed of, for example, a hard resin such as polycarbonate. The housing 18 includes: a first outer surface 30a (outer surface of the first case 30) on a side where the blood inflow chamber 20 is located; and a second outer surface 32a (outer surface of the second case 32) on a side where the blood outflow chamber 22 is located.

As illustrated in FIG. 2, peripheral edge portions of the first case 30 and the second case 32 are joined together by welding (ultrasonic welding or the like) over the entire circumference. In order to facilitate the flow of blood into the blood inflow chamber 20, a plurality of protrusions 34 is provided on the inner surface of the first case 30 facing the filter member 24. In order to facilitate the flow of post-separation blood into the blood outflow chamber 22, a plurality of protrusions 36 is provided on the inner surface of the second case 32 facing the filter member 24. At least one of the protrusion 34 and the protrusion 36 may be omitted.

The filter member 24 is provided between the first case 30 and the second case 32. The filter member 24 is a member that partitions the interior of the housing 18 into the blood inflow chamber 20 and the blood outflow chamber 22 in the up-down direction, and that, at the same time, serves as a flow path when the blood inside the blood inflow chamber 20 moves to the blood outflow chamber 22, thereby separating or removing a predetermined blood component. Specifically, the filter member 24 includes a plurality of identical shaped filter media 38 being stacked in the thickness direction.

The filter medium 38 is formed of a sheet-like porous material having a large number of minute continuous pores communicating from one side to the other side. Examples of such a porous material include a sponge sheet formed of polyurethane, and a nonwoven fabric. The number of stacked sheets of the filter medium 38 is, for example, about two to ten. Note that the filter member 24 of FIG. 2 has six filter media 38 being stacked. The number of filter media 38 constituting the filter member 24 may be one.

In order to prevent blood from flowing from the blood inflow chamber 20 to the blood outflow chamber 22 via the outside of the filter member 24, the peripheral edge portion of the filter member 24 is crimped by a first protrusion 40 provided in the first case 30 and a second protrusion 42 provided in the second case 32 so as to compress the filter member 24 inward in the stacking direction. Each of the first protrusion 40 and the second protrusion 42 extends one round along the peripheral edge portion of the filter member 24.

The blood inflow chamber 20 is formed between the first case 30 and the filter member 24, and the blood outflow chamber 22 is formed between the second case 32 and the filter member 24.

The inflow port 26 is located on a side opposite to the outflow port 28 across a center-of-gravity line Lg passing through center-of-gravity G of the blood separation filter 10A and extending in the thickness direction. The inflow port 26 allows blood to flow into the housing 18, and includes an inflow hole 26a communicating with the blood inflow chamber 20. The inflow port 26 is provided integrally with an outer edge portion of the first case 30. Alternatively, however, the inflow port 26 configured as a member separate from the first case 30 may be joined to the first case 30 by welding or the like.

The outflow port 28 allows the post-separation blood to flow out of the housing 18 and includes an outflow hole 28a communicating with the blood outflow chamber 22. The outflow port 28 is provided integrally with an outer edge portion of the second case 32. Alternatively, however, the outflow port 28 configured as a member separate from the second case 32 may be joined to the second case 32 by welding.

The inflow tube 14 is an elongated flexible cylindrical tube connected to the inflow port 26. One end of the inflow tube 14 is connected to a blood bag 52 containing blood via a sealing member 50, while the other end of the inflow tube 14 is connected to the inflow port 26 (refer to FIG. 3).

The outflow tube 16 is an elongated flexible cylindrical tube connected to the outflow port 28. One end of the outflow tube 16 is connected to the outflow port 28, while the other end of the outflow tube 16 is connected to a storage bag 58 containing post-separation blood (refer to FIG. 3).

The center portion of the second outer surface 32a includes an inlet-side retainer 11a to and from which the inflow tube 14 is attachable and detachable. The housing 18 is laid down so as to allow the blood inflow chamber 20 to be positioned below the filter member 24 and the blood outflow chamber 22 to be positioned above the filter member 24 (refer to FIG. 1) in a state where the housing 18 is suspended with the inflow tube 14 being attached to the inlet-side retainer 11a. Furthermore, the housing 18 also comes in an upright state (refer to FIG. 4) such that the outflow port 28 is positioned below the blood outflow chamber 22 in a state where the housing 18 is suspended after the inflow tube 14 is detached from the inlet-side retainer 11a. The inlet-side retainer 11a is configured to be extendable on the center-of-gravity line Lg in a state where the housing 18 is suspended with the inflow tube 14 being mounted to the inlet-side retainer 11a.

The inlet-side retainer 11a is a clip portion having a retainer groove 13 to and from which the inflow tube 14 is attachable and detachable. Specifically, the inlet-side retainer 11a linearly extends from the center portion of the second outer surface 32a toward the inflow port 26. The retainer groove 13 extends over the entire length of the inlet-side retainer 11a. In order to fit the inflow tube 14 into the retainer groove 13 with a moderate force, a groove width w1 of the retainer groove 13 is set to be slightly smaller than the outer diameter (outside diameter) of the inflow tube 14, while a groove depth d of the retainer groove 13 is set to be substantially equal to the outer diameter of the inflow tube 14. Note that the groove width w and the groove depth d of the retainer groove 13 can be set to any size.

The center portion of the first outer surface 30a includes an outlet-side retainer 11b to and from which the outflow tube 16 is attachable and detachable. The outlet-side retainer 11b is configured to be extendable on the center-of-gravity line Lg in a state where the housing 18 is suspended with the outflow tube 16 being mounted to the outlet-side retainer 11b.

The outlet-side retainer 11b is a clip portion having the retainer groove 13 to and from which the outflow tube 16 is attachable and detachable. Specifically, the outlet-side retainer 11b linearly extends from the center portion of the first outer surface 30a toward the outflow port 28. The retainer groove 13 is configured similarly to the retainer groove 13. The inlet-side retainer 11a and the outlet-side retainer 11b extend in mutually opposite directions from the center portion of the housing 18.

Figure 3:
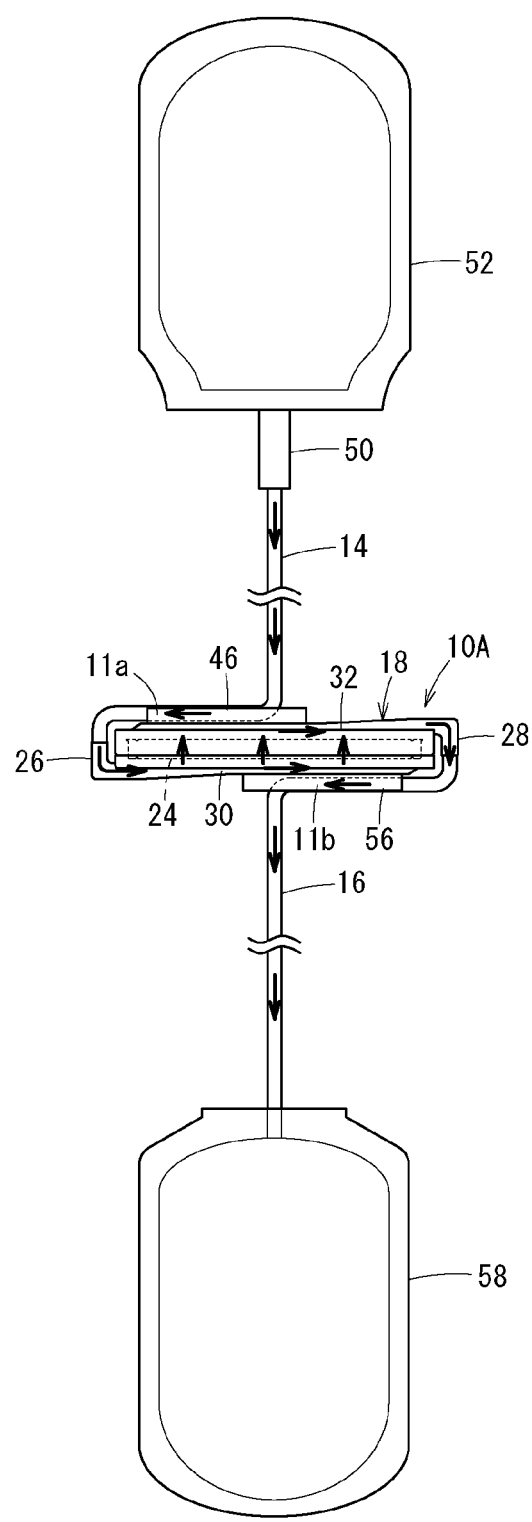
FIG. 3 is a schematic explanatory view of a blood separation method using the blood separation filter of FIG. 1.

Next, a blood separation method using the blood separation filter 10A will be described. As illustrated in FIG. 3, when a predetermined blood component is to be separated from the blood, the blood bag 52 containing blood is first suspended from the suspension base and positioned at a high position. Furthermore, in the arrangement step, the housing 18 is suspended by using the inflow tube 14. With this arrangement, the housing 18 is in a state close to the horizontal state (laid-down state) allowing the blood inflow chamber 20 to be positioned below the filter member 24 and the blood outflow chamber 22 to be positioned above the filter member 24. At this time, at least a portion of the inflow tube 14 and at least a portion of the outflow tube 16 extend on the center-of-gravity line Lg.

Thereafter, a blood treatment step of transferring blood is performed in a state of the arrangement step. Specifically, a sealing member 50 is ruptured, and blood in the blood bag 52 is transferred to the inflow tube 14 by utilizing gravitational force (gravity). The blood transferred to the inflow tube 14 flows into the blood inflow chamber 20 of the housing 18 via the inflow port 26. The blood that has flown into the blood inflow chamber 20 spreads throughout the inside of the blood inflow chamber 20, and the blood liquid level gradually rises. Subsequently, when the blood passes through the filter member 24 upward from below, a blood component (for example, white blood cells) is trapped by the filter member 24, thereby separated or removed from the blood. At this time, the blood is guided from the inflow port 26 to the filter medium 38 from below in the vertical direction, causing the air remaining in the housing 18 to be removed from the outflow port 28. The post-separation blood having passed through the filter member 24 is guided from the inside of the blood outflow chamber 22 to the outflow port 28 and the outflow tube 16, so as to be stored in the storage bag 58.

Figure 4:
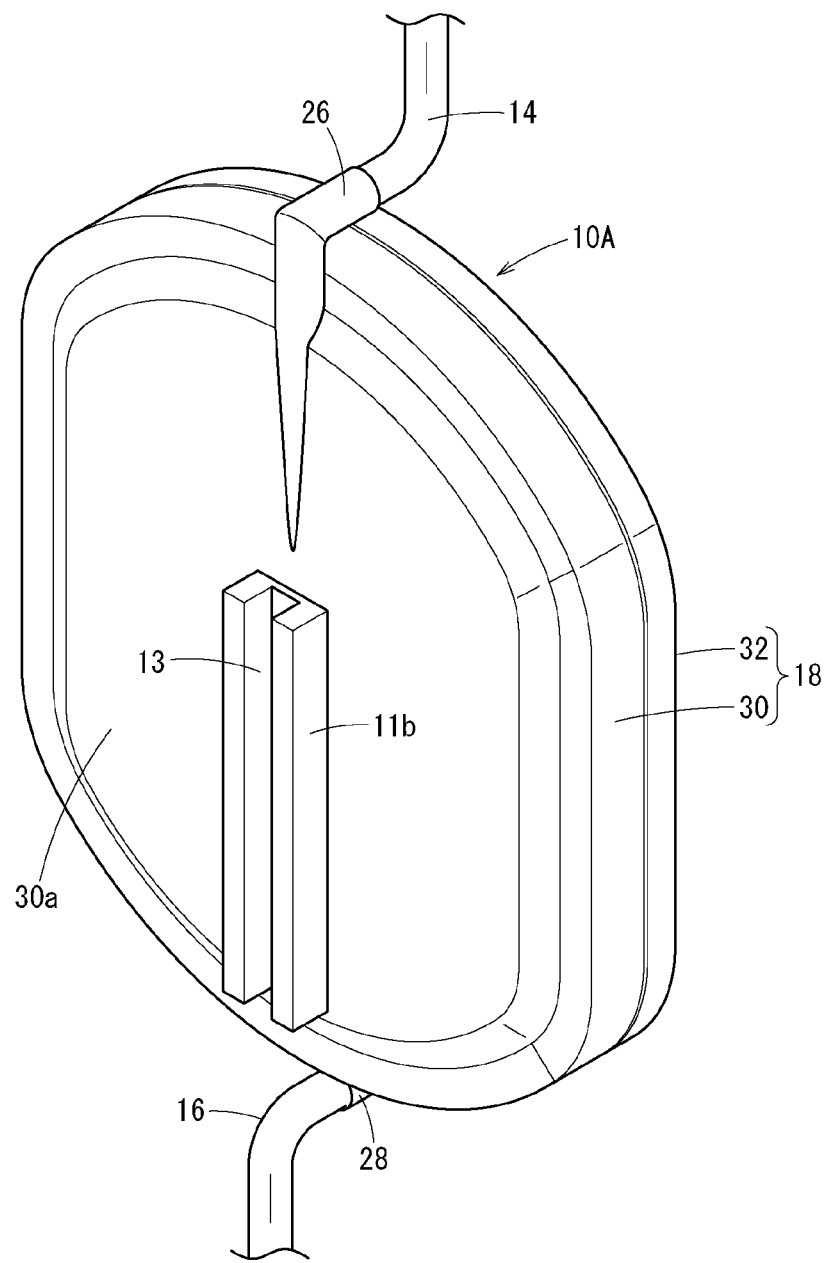
FIG. 4 is a perspective view illustrating a post residual treatment blood collection step of the blood separation filter of FIG. 1.
Figure 5:
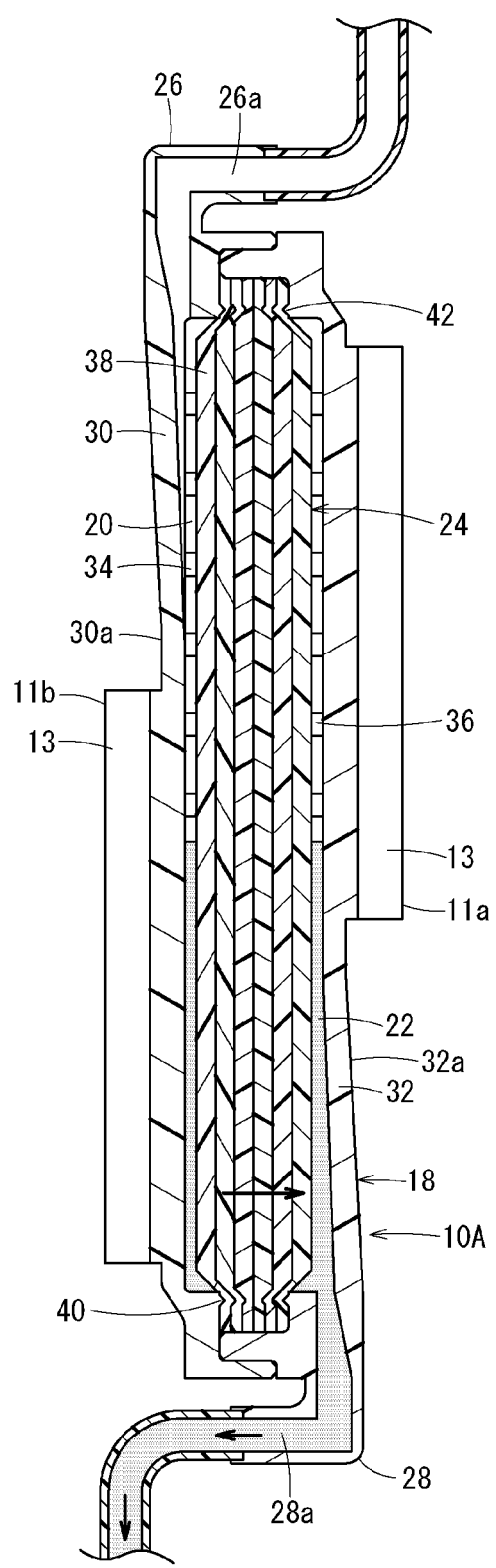
FIG. 5 is a cross-sectional view illustrating a post residual treatment blood collection step of the blood separation filter of FIG. 1.

After completion of the blood treatment step, the inflow tube 14 is detached from the inlet-side retainer 11a and the outflow tube 16 is detached from the outlet-side retainer 11b, as illustrated in FIG. 4, so as to bring the housing 18 into an upright state. At this time, the outflow port 28 is positioned below the blood outflow chamber 22. Accordingly, as illustrated in FIG. 5, the blood in the blood inflow chamber 20 flows downward due to the gravitational force and passes through the lower side of the filter member 24. Subsequently, the post-separation blood guided into the blood outflow chamber 22 is further guided to the outflow tube 16 via the outflow port 28 positioned at the lower side, and stored in the storage bag 58.

Next, effects of the blood separation filter 10A and the blood separation method according to the present embodiment will be described.

The blood separation method is used to separate a predetermined blood component from the blood using the blood separation filter 10A. The blood separation filter 10A includes: a housing 18; a filter medium 38 partitioning the interior of the housing 18 into the blood inflow chamber 20 and the blood outflow chamber 22 in the thickness direction of the housing 18; an inflow port 26 provided in the housing 18 to allow the blood to flow into the blood inflow chamber 20; and an outflow port 28 provided in the housing 18 to allow the post-separation blood from which a blood component has been separated by the filter member 24 to flow out from the interior of the blood outflow chamber 22.

The inflow port 26 is connected with the inflow tube 14. The housing 18 includes the inlet-side retainer 11a to which the inflow tube 14 is detachably attached. In a state where the inflow tube 14 is mounted to the inlet-side retainer 11a, the housing 18 is arranged such that the blood inflow chamber 20 is positioned below the filter medium 38 and the blood outflow chamber 22 is positioned above the filter medium 38. Furthermore, the housing 18 is arranged so that the outflow port 28 is positioned vertically below the blood outflow chamber 22 in a state where the inflow tube 14 is detached from the inlet-side retainer 11a.

In addition, the arrangement step arranges the housing 18 such that the blood inflow chamber 20 is positioned vertically below the filter medium 38 and the blood outflow chamber 22 is positioned vertically above the filter medium 38. In addition, in the blood treatment step, blood is allowed to flow from the inflow port 26 into the blood inflow chamber 20 in the state of the arrangement step, and then, the blood is allowed to pass through the interior of the filter medium 38 upward from vertically below, and then the post-separation blood inside the blood outflow chamber 22 is allowed to flow out to the outflow port 28. Thereafter, the post residual treatment blood collection step arranges the housing 18 such that the outflow port 28 is positioned vertically below the blood outflow chamber 22, thereby guiding the post-separation residual blood in the housing 18 to the outflow port 28.

With this configuration, the blood flowing into the blood inflow chamber 20 from the inflow port 26 spreads to the entire portions inside the blood inflow chamber 20, and then the blood liquid level rises to come in contact with substantially the entire surface (lower surface) of the filter medium 38. Thereafter, the blood passes through the filter medium 38 upward from below so as to be guided to the blood outflow chamber 22. This makes it possible to suppress nonuniformity of blood in the blood inflow chamber 20. In addition, it is possible to reliably discharge the air from the blood inflow chamber 20, leading to suppression of occurrence of air block. Accordingly, this makes it possible to prevent the reduction of the effective area of the filter medium. In addition, the housing 18 is kept upright after the blood treatment step, making it possible to efficiently collect the post-separation residual blood in the housing 18.

In the arrangement step, the housing 18 is arranged in a state where the inflow tube 14 is mounted to the inlet-side retainer 11a. In the post residual treatment blood collection step, the inflow tube 14 is detached from the inlet-side retainer 11a, thereby arranging the housing 18. This makes it possible to easily switch the state of the housing 18 from the laid-down state to the upright state.

The inlet-side retainer 11a is provided at the center portion of the second outer surface 32a of the housing 18 on a side where the blood outflow chamber 22 is located. In the arrangement step, at least a portion of the inflow tube 14 extends on the center-of-gravity line Lg in a state where the inflow tube 14 is mounted to the inlet-side retainer 11a. With this configuration, it is possible to arrange the housing 18 in a laid-down state close to the horizontal posture in the arrangement step.

The center portion of the first outer surface 30a of the housing 18 on a side where the blood inflow chamber 20 is located includes an outlet-side retainer 11b to which the outflow tube 16 connected to the outflow port 28 is detachably attached. In the arrangement step, at least a portion of the outflow tube 16 extends on the center-of-gravity line Lg in a state where the outflow tube 16 is mounted to the outlet-side retainer 11b. With this configuration, it is possible to arrange the housing 18 in a laid-down state closer to the horizontal posture in the arrangement step.

In the post residual treatment blood collection step, the outflow tube 16 is detached from the outlet-side retainer 11b. This makes it possible to efficiently collect the post-separation residual blood in the housing 18 via the outflow tube 16.

The inlet-side retainer 11a is a clip portion including the retainer groove 13 to and from which the inflow tube 14 is attachable and detachable. The outlet-side retainer 11b is a clip portion including the retainer groove 13 to and from which the outflow tube 16 is attachable and detachable. Accordingly, the inflow tube 14 can be attached or detached to or from the inlet-side retainer 11a with a simple configuration, and the outflow tube 16 can be attached or detached to or from the outlet-side retainer 11b with a simple configuration.

Second Embodiment

Next, a blood separation filter 10B according to a second embodiment of the present invention will be described. Note that the second embodiment puts the same reference numerals to the same components as those of the first embodiment, and the description thereof will be omitted.

Figure 6:
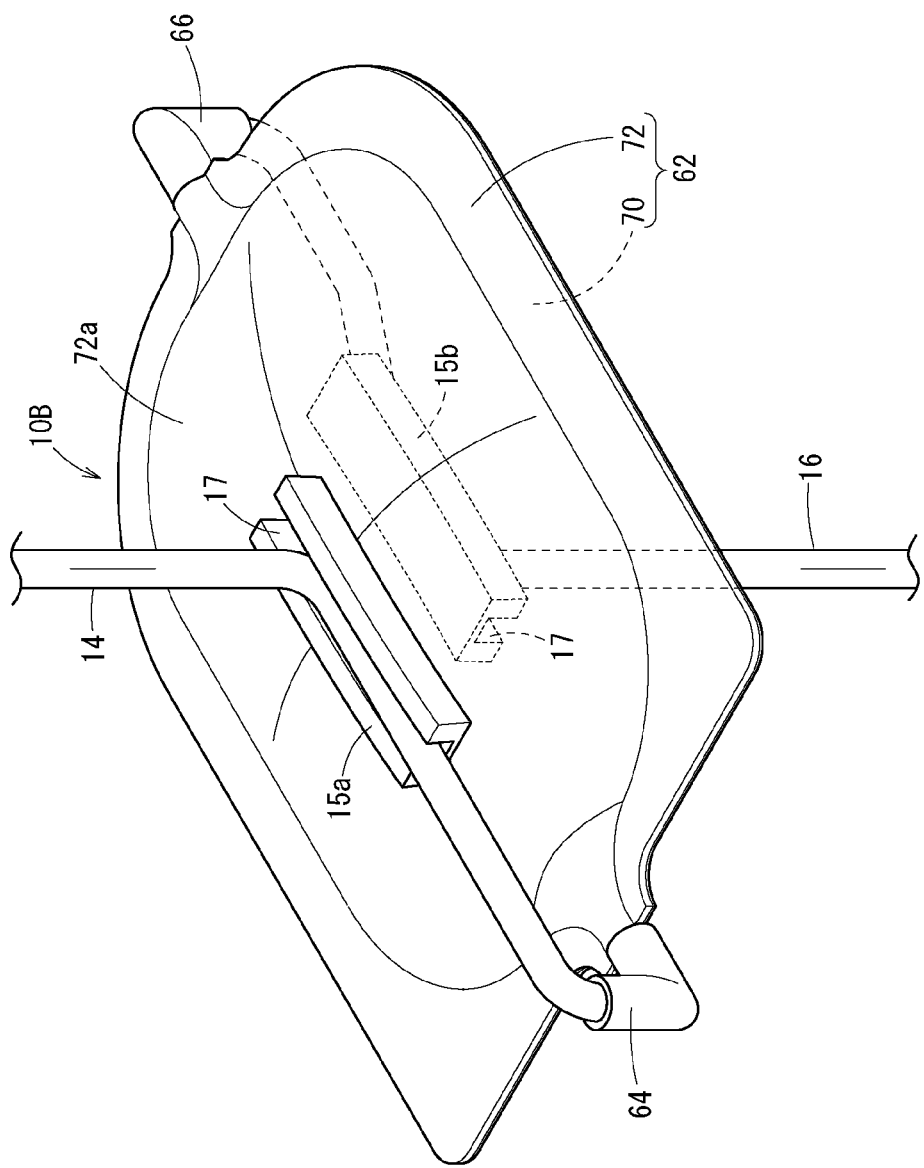
FIG. 6 is a perspective view of a blood separation filter according to a second embodiment of the present invention.
Figure 7:
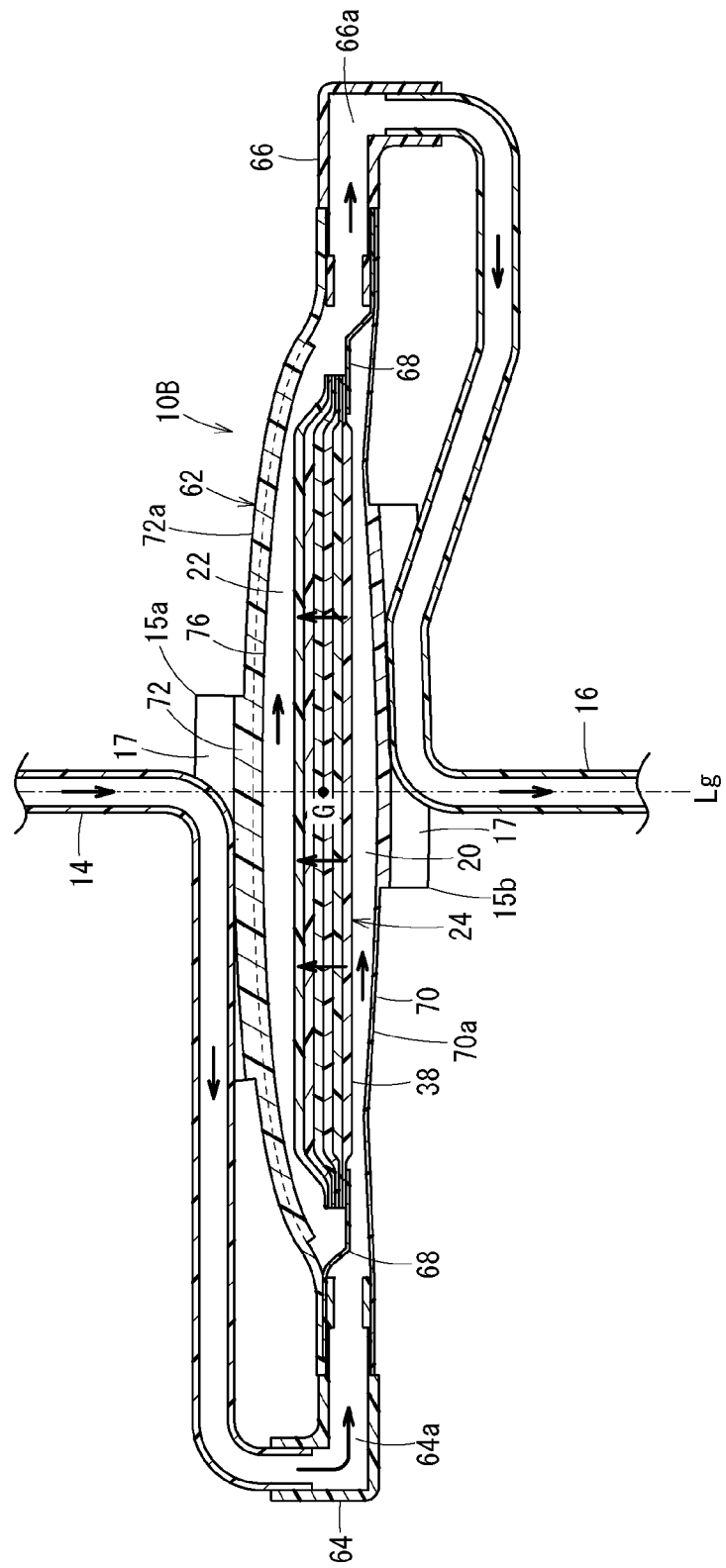
FIG. 7 is a longitudinal sectional view of the blood separation filter of FIG. 6.
Figure 8:
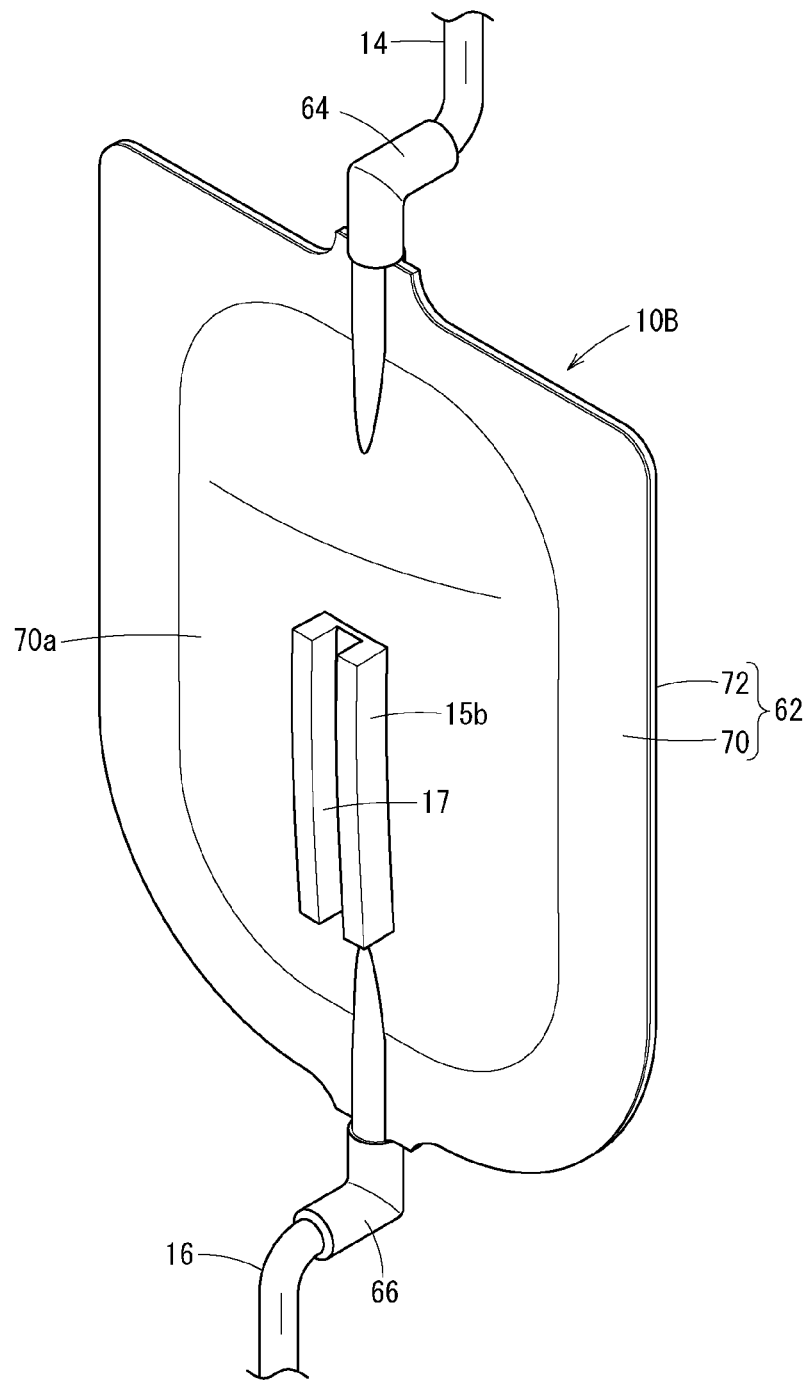
FIG. 8 is a perspective view illustrating a post residual treatment blood collection step of the blood separation filter of FIG. 6.

As illustrated in FIGS. 6 and 7, the blood separation filter 10B includes: a housing 62; the filter member 24 that partitions the interior of the housing 62 in thickness direction into the blood inflow chamber 20 and the blood outflow chamber 22 and that includes the filter medium 38; an inflow port 64 that guides blood into the blood inflow chamber 20; an outflow port 66 to which the post-separation blood is guided from the interior of the blood outflow chamber 22; and a connection sheet 68 extending outward from the filter member 24.

The housing 62 has a shape in a plan view in which one of short sides of a rectangle protrudes in an arc shape. That is, the housing 62 extends in a planar shape. The housing 62 is formed in a bag shape and includes a pair of resin sheets (a first resin sheet 70 and a second resin sheet 72) constituting mutually opposite walls. The first resin sheet 70 and the second resin sheet 72 are formed of soft resin such as polyvinyl chloride, for example. The housing 62 includes: a first outer surface 70a (outer surface of the first resin sheet 70) on a side where the blood inflow chamber 20 is located; and a second outer surface 72a (outer surface of the second resin sheet 72) on a side where the blood outflow chamber 22 is located.

Peripheral edge portions of the first resin sheet 70 and the second resin sheet 72 are joined with each other by welding (radio-frequency welding or the like) via the connection sheet 68 in the entire circumference excluding the inflow port 64 and the outflow port 66.

In order to facilitate the flow of the post-separation blood into the blood outflow chamber 22, a plurality of ribs 76 extending in the longitudinal direction of the second resin sheet 72 is provided on the inner surface of the second resin sheet 72 facing the filter member 24. Note that a plurality of ribs similar to the ribs 76 may be provided on the inner surface of the first resin sheet 70 facing the filter member 24 in order to facilitate the blood flow into the blood inflow chamber 20. In the second resin sheet 72, the ribs 76 may be omitted.

The blood inflow chamber 20 is formed between the first resin sheet 70 and the filter member 24 of the housing 62, while the blood outflow chamber 22 is formed between the second resin sheet 72 and the filter member 24 of the housing 62.

The inflow port 64 is located on a side opposite to the outflow port 66 across the center-of-gravity line Lg passing through the center-of-gravity G of the blood separation filter 10B. The inflow port 64 allows blood to flow into the housing 62, and includes an inflow hole 64a communicating with the blood inflow chamber 20. The inflow port 64 is formed of a soft resin such as polyvinyl chloride. At the outer edge portion of the housing 62, the inflow port 64 is joined to the first resin sheet 70 and the second resin sheet 72 so as to be sandwiched between these sheets by welding.

The outflow port 66 allows the post-separation blood to flow out of the housing 62 and includes an outflow hole 66a communicating with the blood outflow chamber 22. The outflow port 66 is formed of a soft resin such as polyvinyl chloride. At the outer edge portion of the housing 62, the outflow port 66 is joined to the first resin sheet 70 and the second resin sheet 72 so as to be sandwiched between these sheets by welding.

The second outer surface 72a includes an inlet-side retainer 15a to and from which the inflow tube 14 is attachable and detachable. The inlet-side retainer 15a is configured similarly to the inlet-side retainer 11a of the first embodiment. That is, the inlet-side retainer 15a is a clip portion having the retainer groove 17 to and from which the inflow tube 14 is attachable and detachable and extends linearly from the center portion of the second outer surface 72a toward the inflow port 64.

The first outer surface 70a includes an outlet-side retainer 15b to and from which the outflow tube 16 is attachable and detachable. The outlet-side retainer 15b is configured similarly to the outlet-side retainer 15b of the first embodiment. That is, the outlet-side retainer 15b is a clip portion having the retainer groove 17 to and from which the outflow tube 16 is attachable and detachable and extends linearly from the center portion of the first outer surface 70a toward the outflow port 66. The present embodiment has effects similar to those of the first embodiment.

Third Embodiment

Next, a blood separation filter 10C according to a third embodiment of the present invention will be described. Note that the third embodiment puts the same reference numerals to the same components as those of the above-described first embodiment, and the description thereof will be omitted.

As illustrated in FIGS. 9A and 9B, the blood separation filter 10C according to the third embodiment includes: the housing 18; an inlet-side retainer 19a provided in a center portion of the second outer surface 32a of the second case 32; and an outlet-side retainer 19b provided at a center portion of the first outer surface 30a of the first case 30. The inlet-side retainer 19a is a hook portion capable of hooking the inflow tube 14. The inlet-side retainer 19a includes: a retainer base 80 protruding from the center portion of the second outer surface 32a; and a retainer main body 82 extending in an arc shape from the protruding end portion of the retainer base 80. The retainer main body 82 is formed by bending a wire rod in an arc shape.

The angle in the circumferential direction in which the retainer main body 82 extends (range in the circumferential direction in which the retainer main body 82 extends) is preferably in a range of 180° or more and 300° or less, and more preferably 270°. In this case, the inflow tube 14 can be easily attached to and detached from the inlet-side retainer 19a, and the inflow tube 14 can be reliably hooked to the retainer main body 82. However, the angle in the circumferential direction in which the retainer main body 82 extends can be set to any angle. Furthermore, an extending end of the retainer main body 82 is rounded so as not to damage the inflow tube 14.

The inflow tube 14 is inserted into an inner hole 82a constituted on the retainer main body 82. The diameter of the inner hole 82a of the retainer main body 82 is formed to be substantially equal to the outer diameter of the inflow tube 14. A width w2 of an opening 83 between the extending end of the retainer main body 82 and the retainer base 80 is narrower than the outer diameter of the inflow tube 14. This makes it possible to easily suppress detachment of the inflow tube 14 from the inlet-side retainer 19a. In this case, the inflow tube 14 goes through the opening 83 between the retainer main body 82 and the retainer base 80 in a state where the inflow tube 14 is inwardly bent in the radial direction, whereby the attachment and detachment of the inflow tube 14 to and from the inlet-side retainer 19a is performed.

The outlet-side retainer 19b is configured similarly to the inlet-side retainer 19a, and thus, its description will be omitted. According to the present embodiment, the inflow tube 14 can be attached or detached to or from the inlet-side retainer 19a with a simple configuration, and the outflow tube 16 can be attached or detached to or from the outlet-side retainer 19b with a simple configuration.

Fourth Embodiment

Next, a blood separation filter 10D according to a fourth embodiment of the present invention will be described. Note that the fourth embodiment puts the same reference numerals to the same components as those of the above-described second and third embodiments, and the description thereof will be omitted.

Figure 10:
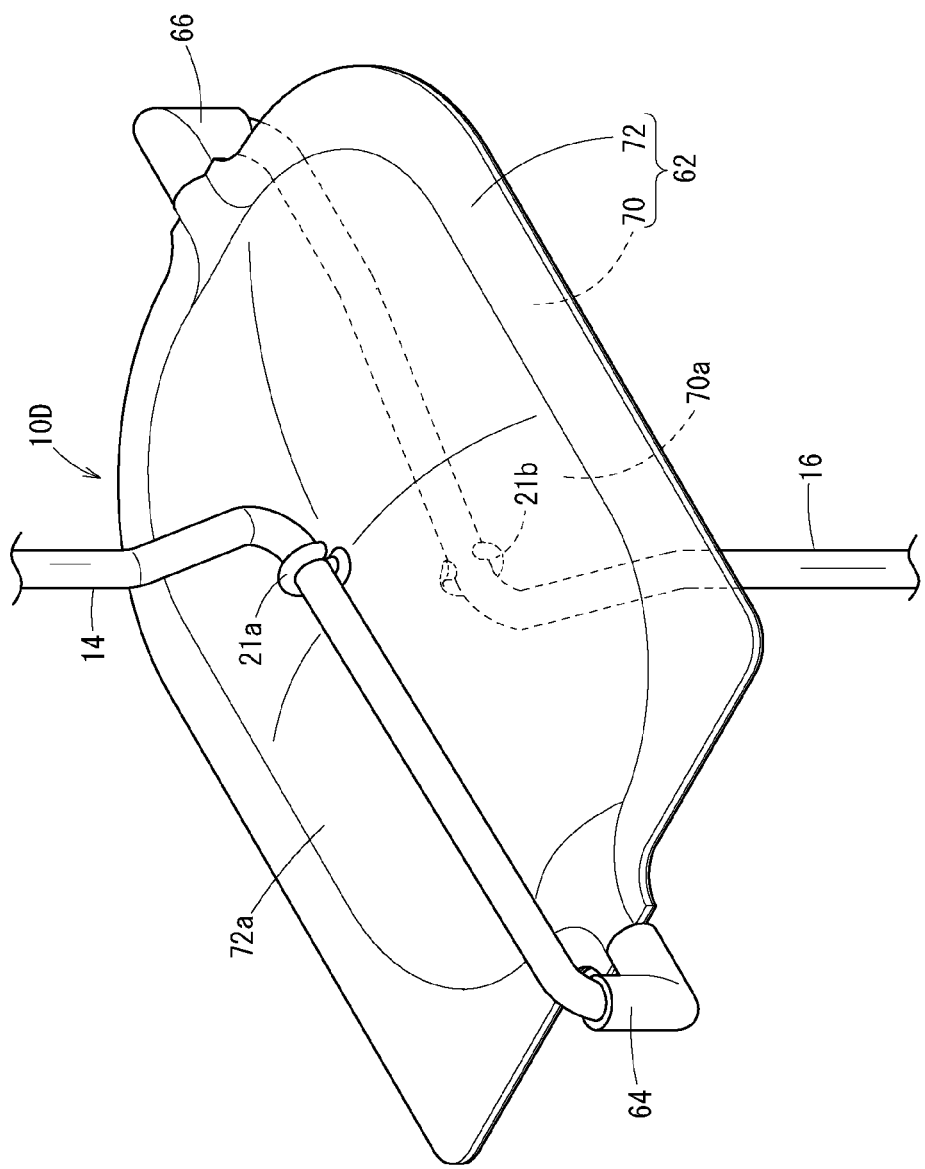
FIG. 10 is a perspective view of a blood separation filter according to a fourth embodiment of the present invention.

As illustrated in FIG. 10, the blood separation filter 10D according to the fourth embodiment includes: the housing 62; an inlet-side retainer 21a provided in a center portion of the second outer surface 32a of the second resin sheet 72, an outlet-side retainer 21b provided on the first outer surface 30a of the first resin sheet 70. The inlet-side retainer 21a is a hook portion capable of hooking the inflow tube 14, and is configured similarly to the inlet-side retainer 19a of the third embodiment.

The outlet-side retainer 21b is a hook portion capable of hooking the outflow tube 16 and is configured similarly to the outlet-side retainer 19b of the third embodiment. The present embodiment has effects similar to those of the third embodiment.

Fifth Embodiment

Next, a blood separation filter 10E according to a fifth embodiment of the present invention will be described. Note that the fifth embodiment puts the same reference numerals to the same components as those of the above-described first embodiment, and the description thereof will be omitted.

Figure 11:
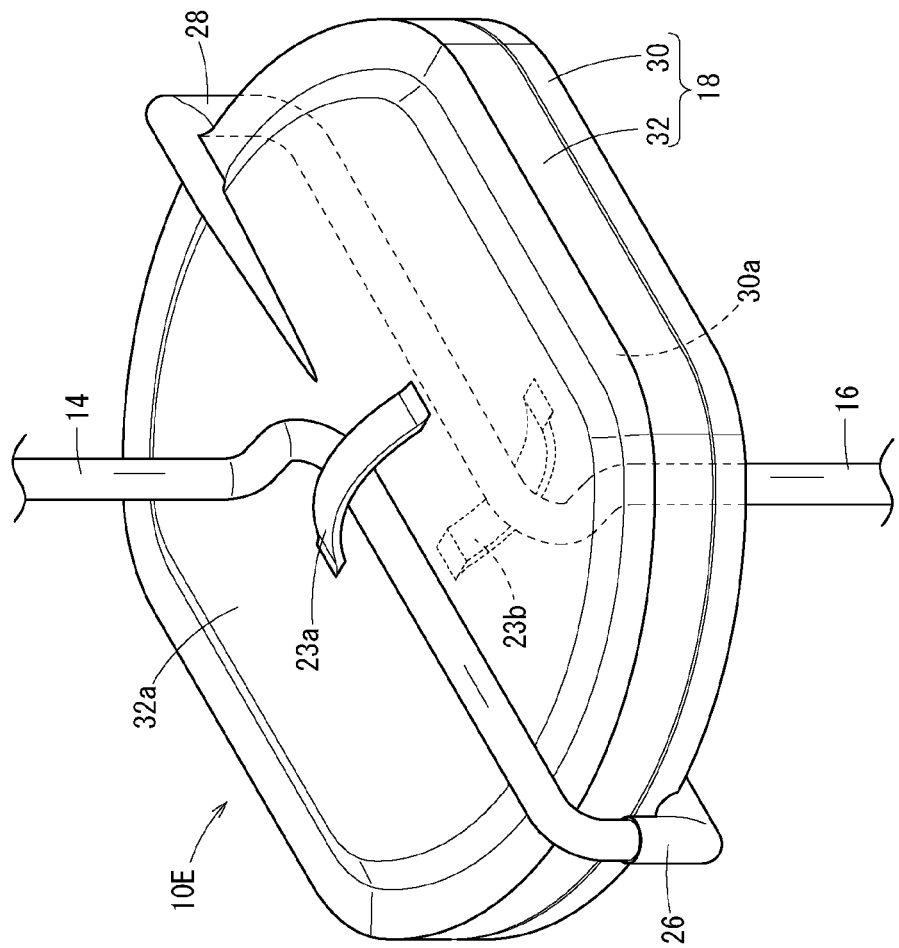
FIG. 11 is a perspective view of a blood separation filter according to a fifth embodiment of the present invention.

As illustrated in FIG. 11, the blood separation filter 10E includes: the housing 18; an inlet-side retainer 23a provided in a center portion of the second outer surface 32a of the second case 32; and an outlet-side retainer 23b provided at a center portion of the first outer surface 30a of the first case 30. The inlet-side retainer 23a is a strip-shaped member that is removably joined to the housing 18 so as to form, between the retainer 23a and the housing 18, a space through which the inflow tube 14 can be inserted. The inlet-side retainer 23a is bent in a direction opposite to the second outer surface 32a.

Both end portions of the inlet-side retainer 23a are welded to the second outer surface 32a of the housing 18. The joining strength between the inlet-side retainer 23a and the housing 18 is set to such a magnitude that the inlet-side retainer 23a can be torn off (removed) with respect to the housing 18 by hand. Note that the inlet-side retainer 23a may be removably joined to the second outer surface 32a by an adhesive or the like.

The outlet-side retainer 23b is a strip-shaped member that is removably joined to the housing 18 so as to form, between the retainer 23b and the housing 18, a space through which the outflow tube 16 can be inserted. The outlet-side retainer 23b is configured similarly to the inlet-side retainer 23a. According to the present embodiment, the inflow tube 14 can be detachably attached to the inlet-side retainer 23a with a simple configuration, while the outflow tube 16 can be detachably attached to the outlet-side retainer 23b with a simple configuration.

Sixth Embodiment

Next, a blood separation filter 10F according to a sixth embodiment of the present invention will be described. Note that the sixth embodiment puts the same reference numerals to the same components as those of the above-described second embodiment, and the description thereof will be omitted.

Figure 12:
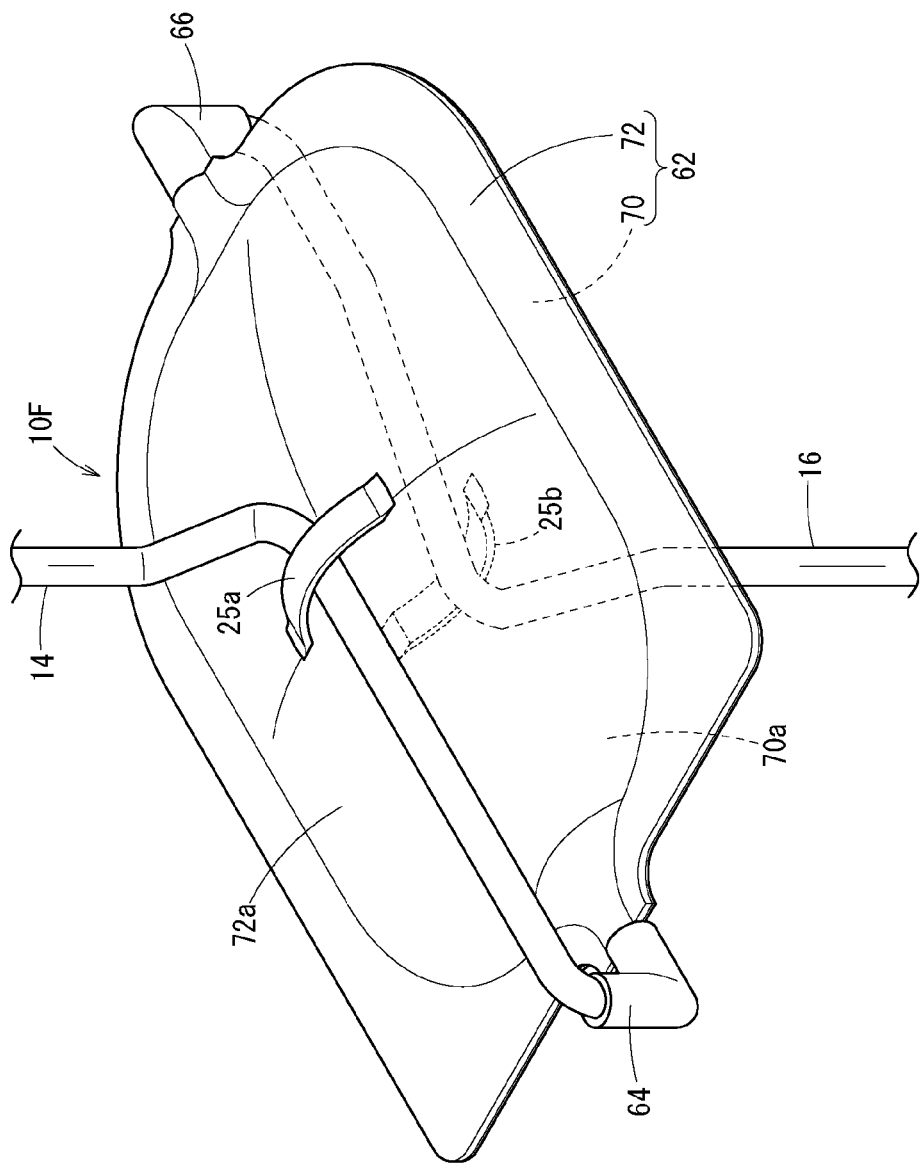
FIG. 12 is a perspective view of a blood separation filter according to a sixth embodiment of the present invention.

As illustrated in FIG. 12, the blood separation filter 10F according to the sixth embodiment includes: the housing 62; an inlet-side retainer 25a provided in a center portion of the second outer surface 32a of the second resin sheet 72, an outlet-side retainer 25b provided on the first outer surface 30a of the first resin sheet 70. The inlet-side retainer 25a is a strip-shaped member that is removably joined to the housing 62 so as to form, between the retainer 25a and the housing 62, a space through which the inflow tube 14 can be inserted. The inlet-side retainer 25a is configured similarly to the inlet-side retainer 25a. The outlet-side retainer 25b is a strip-shaped member that is removably joined to the housing 62 so as to form, between the retainer 25b and the housing 62, a space through which the outflow tube 16 can be inserted. The outlet-side retainer 25b is configured similarly to the inlet-side retainer 25a. The present embodiment has effects similar to those of the fifth embodiment.

The blood separation method and the blood separation filter according to the present invention are not limited to the above-described embodiments, and various configurations can be adopted without departing from the scope and spirits of the present invention.

The invention claimed is:
1. A blood separation method using a blood separation filter that separates a predetermined blood component from blood, the blood separation filter including:
- a housing;
- a filter medium disposed in the housing and partitioning the housing into a blood inflow chamber and a blood outflow chamber in a thickness direction of the housing;
- an inflow port provided in the housing to allow blood to flow into the blood inflow chamber; and
- an outflow port provided in the housing to allow post-separation blood from which a blood component has been separated by the filter medium to flow out from the blood outflow chamber, the blood separation method comprising:
- an arrangement step of arranging the housing such that the blood inflow chamber is positioned vertically below the filter medium and the blood outflow chamber is positioned vertically above the filter medium;
- a blood treatment step of first allowing the blood to flow from the inflow port into the blood inflow chamber in a state of the arrangement step, allowing the blood to flow through an inside of the filter medium upward from vertically below, and then allowing the post-separation blood inside the blood outflow chamber to flow out to the outflow port; and
- a post residual treatment blood collection step of arranging the housing such that the outflow port is positioned vertically below the blood outflow chamber after the blood treatment step, thereby guiding post-separation residual blood in the housing, to the outflow port.

2. The blood separation method according to claim 1, wherein the housing includes an inlet-side retainer to which an inflow tube connected to the inflow port is detachably mounted,
the arrangement step arranges the housing in a state where the inflow tube is mounted to the inlet-side retainer, and
the post residual treatment blood collection step arranges the housing by detaching the inflow tube from the inlet-side retainer.

3. The blood separation method according to claim 2, wherein the inlet-side retainer is provided at a center portion of an outer surface of the housing on a side where the blood outflow chamber is located, and
the arrangement step allows at least a portion of the inflow tube to extend on a center-of-gravity line (Lg) passing through center-of-gravity (G) of the blood separation filter in the state where the inflow tube is mounted to the inlet-side retainer.

4. The blood separation method according to claim 3, wherein the housing includes, at a center portion of an outer surface on a side where the blood inflow chamber is located, an outlet-side retainer to which an outflow tube, connected to the outflow port is detachably mounted, and
the arrangement step allows at least a portion of the outflow tube to extend on the center-of-gravity line (Lg) in a state where the outflow tube is mounted to the outlet-side retainer.

5. The blood separation method according to claim 4, wherein the post residual treatment blood collection step detaches the outflow tube from the outlet-side retainer.

6. A blood separation filter that separates a predetermined blood component from blood, the blood separation filter comprising:
- a housing;
- a filter medium disposed in the housing and partitioning an interior of the housing into a blood inflow chamber and a blood outflow chamber in a thickness direction of the housing;
- an inflow port provided in the housing to allow blood to flow into the blood inflow chamber; and
- an outflow port provided in the housing to allow post-separation blood from which a blood component has been separated by the filter medium to flow out from the blood outflow chamber,
- wherein the inflow port is connectable with an inflow tube,
- wherein the housing includes an inlet-side retainer to which the inflow tube is detachably attached,
- wherein the inflow port comprises a first portion that connects to the inflow tube and that includes a flow path that extends in a thickness direction of the filter medium, and a second portion that is in communication with the blood inflow chamber and the first portion of the inflow port and that includes a flow path that extends in a direction substantially perpendicular to the thickness direction of the filter medium,
- wherein, when the blood is introduced into the inflow port,
the blood inflow chamber is positioned vertically below the filter medium and the blood outflow chamber is positioned vertically above the filter medium, and
- wherein, when the post-separation blood flows out of the blood outflow chamber, the outflow port is positioned vertically below the blood outflow chamber.

7. The blood separation filter according to claim 6, wherein the housing includes:
- a first outer surface on a side where the blood inflow chamber is located; and
- a second outer surface on a side where the blood outflow chamber is located,
wherein the inlet-side retainer is provided at a center portion of the second outer surface, and
wherein the inlet-side retainer is configured such that at least a portion of the inflow tube is extendable on a center-of-gravity line (Lg) passing through center-of-gravity (G) of the blood separation filter in a state where the housing is arranged with the inflow tube being mounted to the inlet-side retainer.

8. The blood separation filter according to claim 7, wherein the outflow port is connected with an outflow tube,
wherein an outlet-side retainer to and from which the outflow tube is attachable and detachable is provided at a center portion of the first outer surface, and
wherein the outlet-side retainer is configured such that at least a portion of the outflow tube is extendable on the center-of-gravity line (Lg) in a state where the outflow tube is mounted to the outlet-side retainer.

9. The blood separation filter according to claim 8, wherein at least one of the inlet-side retainer and the outlet-side retainer is a hook portion capable of hooking the inflow tube or the outflow tube.

10. The blood separation filter according to claim 8, wherein at least one of the inlet-side retainer and the outlet-side retainer is a strip-shaped member removably joined to the housing so as to form, between the strip-shaped member and the housing, a space through which the inflow tube or the outflow tube is inserted.

11. The blood separation filter according to claim 8, wherein at least one of the inlet-side retainer and the outlet-side retainer is a clip portion having a retainer groove to and from which the inflow tube or the outflow tube is attachable and detachable.

12. The blood separation filter according to claim 6, wherein the housing further comprises at least one protrusion that compresses the filter medium to block the blood from flowing around the filter medium.

13. The blood separation filter according to claim 12, wherein the at least one protrusion comprises a first protrusion on a first case of the housing and a second protrusion on a second case of the housing.

14. The blood separation filter according to claim 6, wherein the outflow port comprises a first portion that connects to an outflow tube and that includes a flow path that extends in the thickness direction of the filter medium, and a second portion that is in communication with the blood outflow chamber and the first portion of the outflow port and that includes a flow path that extends in the direction substantially perpendicular to the thickness direction of the filter medium, wherein the first and second portions of the inflow port and the first and second portions of the outflow port are at opposite interior edges of the housing.

15. The blood separation filter according to claim 6, wherein the housing comprises a first resin sheet and a second resin sheet joined to one another.

16. The blood separation filter according to claim 15, wherein the housing comprises a connection sheet that joins the first resin sheet and the second resin sheet to the filter medium.

17. The blood separation filter according to claim 16, wherein the connection sheet joins the first resin sheet and the second resin sheet to the filter medium around an entire circumference of the filter medium.

18. The blood separation filter according to claim 15, wherein the housing includes:
 a first outer surface on a side where the blood inflow chamber is located; and
 a second outer surface on a side where the blood outflow chamber is located,
 wherein the inlet-side retainer is provided at a center portion of the second outer surface,
 wherein the inlet-side retainer is configured such that at least a portion of the inflow tube is extendable on a center-of-gravity line (Lg) passing through center-of-gravity (G) of the blood separation filter in a state where the housing is arranged with the inflow tube being mounted to the inlet-side retainer,
 wherein the outflow port is connected with an outflow tube,
 wherein an outlet-side retainer to and from which the outflow tube is attachable and detachable is provided at a center portion of the first outer surface, and
 wherein the outlet-side retainer is configured such that at least a portion of the outflow tube is extendable on the center-of-gravity line (Lg) in a state where the outflow tube is mounted to the outlet-side retainer.

19. The blood separation filter according to claim 18, wherein at least one of the inlet-side retainer and the outlet-side retainer is a clip portion having a retainer groove to and from which the inflow tube or the outflow tube is attachable and detachable.

20. A blood separation filter that separates a predetermined blood component from blood, the blood separation filter comprising:
 a housing;
 a filter medium disposed in the housing and partitioning an interior of the housing into a blood inflow chamber and a blood outflow chamber in a thickness direction of the housing;
 an inflow port provided in the housing to allow blood to flow into the blood inflow chamber; and
 an outflow port provided in the housing to allow post-separation blood from which a blood component has been separated by the filter medium to flow out from the blood outflow chamber,
 wherein the inflow port is connectable with an inflow tube,
 wherein the housing includes an inlet-side retainer to which the inflow tube is detachably attached,
 wherein, when the blood is introduced into the inflow port, the blood inflow chamber is positioned vertically below the filter medium and the blood outflow chamber is positioned vertically above the filter medium,
 wherein, when the post-separation blood flows out of the blood outflow chamber, the outflow port is positioned vertically below the blood outflow chamber
 wherein the housing includes:
  a first outer surface on a side where the blood inflow chamber is located; and
  a second outer surface on a side where the blood outflow chamber is located,
 wherein the inlet-side retainer is provided at a center portion of the second outer surface, and the inlet-side retainer is configured such that at least a portion of the inflow tube is extendable on a center-of-gravity line (Lg) passing through center-of-gravity (G) of the blood separation filter in a state where the housing is arranged with the inflow tube being mounted to the inlet-side retainer,
 wherein the outflow port is connected with an outflow tube,
 wherein an outlet-side retainer to and from which the outflow tube is attachable and detachable is provided at a center portion of the first outer surface, and the outlet-side retainer is configured such that at least a portion of the outflow tube is extendable on the center-of-gravity line (Lg) in a state where the outflow tube is mounted to the outlet-side retainer, and
 wherein at least one of the inlet-side retainer and the outlet-side retainer is a clip portion having a retainer groove to and from which the inflow tube or the outflow tube is attachable and detachable.

* * * * *